United States Patent
Lynch et al.

(10) Patent No.: US 9,115,046 B2
(45) Date of Patent: Aug. 25, 2015

(54) PRODUCTION OF ETHANOL FROM SYNTHESIS GAS

(71) Applicants: David Lynch, Burlington, CT (US);
Esteban Chornet, Sherbrooke (CA);
Charles Bureau, Sherbrooke (CA);
Stephane Marie-Rose, Sherbrooke (CA)

(72) Inventors: David Lynch, Burlington, CT (US);
Esteban Chornet, Sherbrooke (CA);
Charles Bureau, Sherbrooke (CA);
Stephane Marie-Rose, Sherbrooke (CA)

(73) Assignee: Enerkem, Inc., Montreal, Quebec (CA)

( * ) Notice: Subject to any disclaimer, the term of this patent is extended or adjusted under 35 U.S.C. 154(b) by 314 days.

(21) Appl. No.: 13/710,682

(22) Filed: Dec. 11, 2012

(65) Prior Publication Data
US 2013/0178671 A1    Jul. 11, 2013

Related U.S. Application Data

(60) Provisional application No. 61/578,006, filed on Dec. 20, 2011.

(51) Int. Cl.
*C07C 29/10* (2006.01)
*C07C 29/36* (2006.01)
*C07C 41/01* (2006.01)

(52) U.S. Cl.
CPC ............... *C07C 29/36* (2013.01); *C07C 41/01* (2013.01)

(58) Field of Classification Search
CPC .................................................. C07C 29/10
USPC ............................................................ 568/907
See application file for complete search history.

(56) References Cited

U.S. PATENT DOCUMENTS

| 4,415,749 | A | 11/1983 | Hargis et al. |
| 4,424,384 | A | 1/1984 | Lin et al. |
| 4,727,200 | A | 2/1988 | Wegman et al. |
| 5,414,161 | A | 5/1995 | Uhm et al. |
| 8,080,693 | B2 | 12/2011 | Chornet et al. |
| 2011/0124927 | A1 | 5/2011 | Stites et al. |

FOREIGN PATENT DOCUMENTS

| GB | 2162172 | 1/1986 |
| WO | WO83/03409 | 10/1983 |
| WO | WO2009/077720 | 6/2009 |

OTHER PUBLICATIONS

Zhang, et al., Ind. Eng. Chem. Res., vol. 49, pp. 5485-5488 (2010).
Yang, et al., Catalysis Today, vol. 164, pp. 425-428 (2011).

*Primary Examiner* — Elvis O Price
(74) *Attorney, Agent, or Firm* — Raymond J. Lillie

(57) ABSTRACT

A process for producing ethanol from synthesis gas by reacting the hydrogen and carbon monoxide of the synthesis gas to provide methanol, which then is subjected to dehydration to produce at least one ether, such as dimethyl ether. The ether, such as dimethyl ether, then is subjected to carbonylation with unreacted carbon monoxide from the synthesis gas to provide at least one acetate, such as methyl acetate. The acetate then is subjected to hydrogenolysis to produce ethanol.

22 Claims, 1 Drawing Sheet

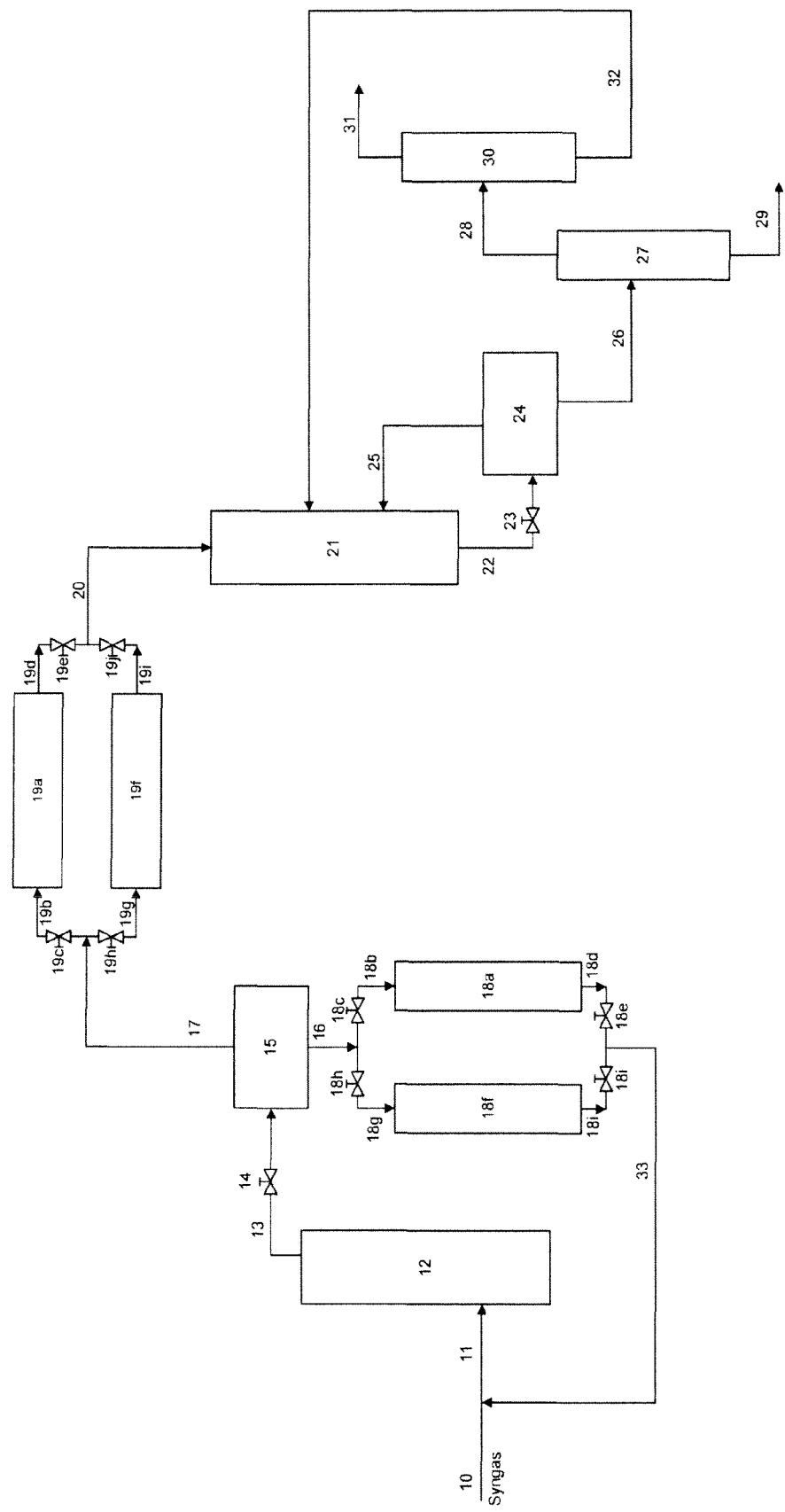

PRODUCTION OF ETHANOL FROM SYNTHESIS GAS

This Application claims priority based on provisional Application Ser. No. 61/578,006, filed Dec. 20, 2011, the contents of which are incorporated by reference in their entirety.

This invention relates to the production of ethanol from synthesis gas. More particularly, this invention relates to producing ethanol from synthesis gas by reacting the hydrogen and carbon monoxide of the synthesis gas to provide a first reaction product that includes at least one ether, unreacted hydrogen, and unreacted carbon monoxide. This reaction product then is reacted under conditions to provide a second reaction product that includes ethanol.

In accordance with an aspect of the present invention, there is provided a process for producing ethanol from synthesis gas. The process comprises reacting synthesis gas, which contains hydrogen and carbon monoxide, under conditions to provide a first product including at least one ether, unreacted hydrogen, and unreacted carbon monoxide. The first reaction product then is reacted under conditions to provide a second reaction product including ethanol.

Ethers which may be included in the first reaction product include, but are not limited to, dimethyl ether and diethyl ether. In a non-limiting embodiment, the at least one ether is dimethyl ether.

In a non-limiting embodiment, the at least one ether is produced by reacting the hydrogen and carbon monoxide in the synthesis gas to produce methanol, and the methanol then is converted to the at least one ether, to provide the first reaction product, including the at least one ether, the unreacted hydrogen, and the unreacted carbon monoxide.

The above-mentioned reactions may be conducted in a single reaction vessel, or in separate reaction vessels.

In another non-limiting embodiment, the above-mentioned reactions may be conducted in the presence of a methanol synthesis catalyst and a dehydration catalyst.

Methanol synthesis catalysts which may be employed include, but are not limited to, copper oxide (CuO), zinc oxide (ZnO), and mixtures thereof.

In another non-limiting embodiment, the dehydration catalyst is gamma-alumina.

In yet another non-limiting embodiment, the hydrogen and carbon monoxide are reacted to provide methanol according to the following reaction equation:

$$CO + 2H_2 \rightarrow CH_3OH$$

The methanol then is subjected to dehydration to produce dimethyl ether according to the following reaction equation:

$$2CH_3OH \rightarrow CH_3OCH_3 + H_2O$$

In a further non-limiting embodiment, the hydrogen and carbon monoxide are reacted in the presence of a catalyst to produce the at least one ether and methanol. The catalyst may be in a fixed bed reactor or may be suspended in an inert oil, such as white mineral oil or Drakeol, into which the hydrogen and carbon monoxide are bubbled. In such an embodiment, the hydrogen and carbon monoxide are reacted in the presence of the catalyst to produce methanol. The methanol then is reacted immediately in the presence of the catalyst to produce the at least one ether, such as dimethyl ether, and water.

In a non-limiting embodiment, the catalyst which catalyzes the reactions that produce methanol, and then at least one ether, is a copper chromite, copper oxide, or zinc oxide catalyst, or mixtures thereof. In another non-limiting embodiment, the catalyst is supported in appropriate support, such as an alumina support, or a zeolite. The support may, in a non-limiting embodiment, be a mesoporous support.

In yet another embodiment, the catalyst further includes a transition metal.

In a non-limiting embodiment, the hydrogen and carbon monoxide of the synthesis gas are reacted at a pressure of from about 250 psi to about 2,000 psi. In another non-limiting embodiment, the hydrogen and carbon monoxide of the synthesis gas are reacted at a pressure of from about 300 psi to about 900 psi.

In a non-limiting embodiment, the hydrogen and carbon monoxide are reacted at a temperature of from about 100° C. to about 400° C. In another non-limiting embodiment, the hydrogen and carbon monoxide are reacted at a temperature of from about 150° C. to about 350° C.

In a non-limiting embodiment, the hydrogen and carbon monoxide are reacted at a molar ratio of hydrogen to carbon monoxide of from about 0.6 to about 3.0.

Alternatively, the hydrogen and carbon monoxide are reacted in the presence of a methanol synthesis catalyst in a first reactor to produce methanol, and the methanol is reacted in the presence of a dehydration catalyst in a second reactor to produce at least one ether, such as dimethyl ether.

As a result of reacting the hydrogen and carbon monoxide of the synthesis gas to produce methanol, followed by the conversion of methanol to at least one ether, such as, for example, by dehydrating the methanol to produce dimethyl ether, there is provided a reaction product that includes at least one ether, (such as dimethyl ether, for example), unreacted hydrogen, and unreacted carbon monoxide. In a non-limiting embodiment, the reaction product further includes unreacted methanol. In another non-limiting embodiment, at least a portion of the unreacted methanol may be recycled such that it is reacted in the presence of a catalyst to produce additional at least one ether, such as dimethyl ether, for example.

In another non-limiting embodiment, the reaction product further includes water. In a non-limiting embodiment, the water is removed from the reaction product prior to reacting the at least one ether to produce ethanol. Such water removal may be effected either by passing the reaction product over a desiccant to remove the water in the vapor phase, or by cooling the reaction product to remove condensed water therefrom.

The reaction product, which includes at least one ether, and unreacted hydrogen and unreacted carbon monoxide from the synthesis gas, then is reacted under conditions to provide a second reaction product that includes ethanol.

In a non-limiting embodiment, the at least one ether is reacted with the carbon monoxide to produce at least one acetate, and the at least one acetate is subjected to hydrogenolysis to produce ethanol.

In a non-limiting embodiment, the at least one ether is dimethyl ether, as hereinabove described. In another non-limiting embodiment, the at least one acetate is selected from the group consisting of methyl acetate, ethyl acetate, and mixtures thereof. In another non-limiting embodiment, the at least one acetate is methyl acetate.

In a non-limiting embodiment, dimethyl ether is reacted with carbon monoxide to produce methyl acetate according to the following equation:

$$CH_3OCH_3 + CO \rightarrow CH_3COOCH_3$$

The methyl acetate then is subjected to hydrogenolysis to produce ethanol and methanol according to the following equation:

$$CH_3COOCH_3 + 2H_2 \rightarrow CH_3OH + CH_3CH_3OH$$

In another non-limiting embodiment, the reaction of the at least one ether to produce at least one acetate, and the reaction of the at least one acetate to produce ethanol are effected in the presence of a carbonylation catalyst and a hydrogenolysis catalyst. Carbonylation catalysts which may be employed include, but are not limited to, zeolite catalysts, such as, for example, H-Mordenite, and Group VII metal catalysts. Hydrogenolysis catalysts which may be employed include, but are not limited to, copper chromite, copper oxide, zinc oxide, and noble metal-based catalysts.

In a non-limiting embodiment, the carbonylation and hydrogenolysis catalysts are contained in one reactor or reaction zone. In another non-limiting embodiment, the carbonylation and hydrogenolysis catalysts are contained in separate reactors or reaction zones.

In a non-limiting embodiment, dimethyl ether, hydrogen, and carbon monoxide are reacted in a reactor, such as, for example, a reactor that contains a plurality of fixed catalyst beds, which contains a carbonylation catalyst and a hydrogenolysis catalyst. In one non-limiting embodiment, the dimethyl ether, hydrogen, and carbon monoxide are passed to the reactor at a molar ratio of carbon monoxide to dimethyl ether of from about 1:1 to about 20:1 and a molar ratio of hydrogen to dimethyl ether of from about 1:1 to about 20:1. In another non-limiting embodiment, the dimethyl ether, hydrogen, and carbon monoxide are passed to the reactor at a molar ratio of carbon monoxide to dimethyl ether of from about 5:1 to about 10:1 and a molar ratio of hydrogen to dimethyl ether of from about 5:1 to about 10:1. In another non-limiting embodiment, the dimethyl ether, hydrogen, and carbon monoxide are passed through the reactor at a gas hourly space velocity (GHSV) of from about 250 1/h to about 20,000 1/h liters of carbon monoxide per liter of catalyst, for total gas measured at standard temperature and pressure (STP) conditions. In yet another non-limiting embodiment, the dimethyl ether, hydrogen, and carbon monoxide are passed through the reactor at a gas hourly space velocity (GHSV) of from about 2,000 1/h to about 8,000 1/h liters of carbon monoxide per liter of catalyst, for total gas measured at standard temperature and pressure (STP) conditions. In yet another non-limiting embodiment, the dimethyl ether, hydrogen, and carbon monoxide are reacted at a temperature of from about 100° C. to about 300° C. In a further non-limiting embodiment, the dimethyl ether, hydrogen, and carbon monoxide are reacted at a temperature of from about 225° C. to about 275° C. In a further non-limiting embodiment, the hydrogen and carbon monoxide are passed to the reactor at a molar ratio of hydrogen to carbon monoxide of from about 0.6 to about 3.0.

Thus, dimethyl ether, hydrogen, and carbon monoxide are reacted in the reactor in the presence of a carbonylation catalyst and a hydrogenolysis catalyst. In the reactor, dimethyl ether is reacted with carbon monoxide to produce at least one acetate, such as methyl acetate, for example. The at least one methyl acetate then immediately is subjected to hydrogenolysis to produce a reaction product that includes ethanol. In a non-limiting embodiment, the reaction product further includes unreacted hydrogen and unreacted carbon monoxide. The unreacted hydrogen and unreacted carbon monoxide, which is in the form of synthesis gas, may be separated from the reaction product and be recycled to the carbonylation/hydrogenolysis reactor, to be reacted with fresh dimethyl ether and fresh acetate to provide additional ethanol.

In another non-limiting embodiment, the reaction product further includes at least one acetate, such as methyl acetate and/or ethyl acetate. In yet another non-limiting embodiment, the reaction product further includes methanol.

In another non-limiting embodiment, the dimethyl ether, and the hydrogen and carbon monoxide are reacted in a first, or carbonylation, reactor, which contains a carbonylation catalyst, to provide a product that includes at least one acetate, such as methyl acetate and/or ethyl acetate, and hydrogen, and also may include unreacted carbon monoxide. This reaction product is passed to a second, or hydrogenolysis, reactor, which contains a hydrogenolysis catalyst, to produce a reaction product that includes ethanol. The reaction product also may include methanol, and at least one unreacted acetate, such as methyl acetate and/or ethyl acetate.

In a non-limiting embodiment, the carbonylation reactor is operated under the molar ratios of carbon monoxide to dimethyl ether, hydrogen to dimethyl ether, and hydrogen to carbon monoxide hereinabove described, as well as the GHSV and temperature conditions hereinabove described.

In the second, or hydrogenolysis, reactor, the at least one acetate, such as methyl acetate, is reacted with hydrogen to produce a product which includes ethanol. In a non-limiting embodiment, the at least one acetate is reacted with the hydrogen at a temperature of from about 150° C. to about 300° C. In another non-limiting embodiment, the at least one acetate is reacted with the hydrogen at a temperature of from about 170° C. to about 275° C. In yet another non-limiting embodiment, the at least one acetate is reacted with the hydrogen at a temperature of from about 225° C. to about 275° C.

In another non-limiting embodiment, the at least one acetate, such as methyl acetate, is reacted with hydrogen at a molar ratio of hydrogen to acetate of at least 3. In another non-limiting embodiment, the at least one acetate is reacted with hydrogen at a molar ratio of hydrogen to acetate of from about 5 to about 10.

The invention now will be described with respect to the drawing, wherein:

The drawing is a schematic of an embodiment of the process of the present invention.

Referring now to the drawing, conditioned synthesis gas in line 10 is mixed with recycled methanol from line 33, and the synthesis gas and recycled methanol are passed through line 11 to dimethyl ether reactor 12. Reactor 12 contains a catalyst that is able to convert the synthesis gas into dimethyl ether after a single pass through reactor 12.

In reactor 12, the carbon monoxide and hydrogen of the synthesis gas are reacted to produce methanol, and the methanol then is subjected to dehydration to produce dimethyl ether. Dimethyl ether, unreacted synthesis gas, unconverted methanol, and water are withdrawn from reactor 12 through line 13, and passed through line 13 and valve 14 to condenser 15. In condenser 15, the water and methanol, which are in the vapor phase, are condensed, and are withdrawn from condenser 15 through line 16 and passed to water removal zone 18.

Water removal zone 18 includes two desiccators, 18a and 18f, each of which contains an appropriate desiccant. During operation, the desiccant in one of the desiccators 18a and 18f removes water from the mixture of water and methanol, while the desiccant in the other of desiccators 18a and 18f is being regenerated, i.e., the water is being removed from the desiccant. For example, the mixture of water and unconverted methanol from line 16 is passed through line 18b and open valve 18c to desiccator 18a, in which water is removed from the methanol. The dried methanol then is withdrawn from desiccator 18a, and passed through line 18d and open valve 18e to line 33. During this time, valves 18h and 18j are closed. When the desiccant in desiccators 18a is saturated with water, valves 18c and 18e are closed, and valves 18h and 18j are opened. Water and methanol from line 16 are passed through line 18g and valve 18h to desiccator 18f, in which water is removed from the methanol. The dried methanol then is withdrawn from desiccator 18f, and passed through line 18i and valve 18j to line 33. When the desiccant in desiccator 18f becomes saturated with water, valves 18h and 18j are closed, and valves 18c and 18e are opened. The methanol, which is passed to line 33 from line 18d or line 18i, then is passed through line 33 to line 11, where it is combined with synthesis gas from line 10, and then is recycled to reactor 12.

Dimethyl ether, unreacted synthesis gas, and trace amounts of water are withdrawn from condenser 15 through line 17 and passed to water removal zone 19. The dimethyl ether, synthesis gas, and trace amounts of water are passed through line 19b, valve 19c, desiccator 19a, line 19d, and valve 19e, or are passed through line 19g, valve 19h, desiccator 19f, line 19i, and valve 19j.

In desiccator 19a or desiccator 19f, water is removed from the dimethyl ether and synthesis gas. The dimethyl ether and synthesis gas in line 19d or line 19i then is passed through line 20 to carbonylation/hydrogenolysis reactor 21. Reactor 21 is contains a plurality of fixed catalyst beds and contains carbonylation and hydrogenolysis catalysts.

In reactor 21, the dimethyl ether and synthesis gas are subjected to carbonylation and hydrogenolysis to provide a reaction production that includes ethanol, methanol, methyl acetate, and ethyl acetate, as well as unreacted dimethyl ether and unconverted synthesis gas. The reaction product is withdrawn from reactor 21, and passed through line 22 and valve 23 to condenser 24. In condenser 24, the ethanol, methanol, methyl acetate, and ethyl acetate are separated from the unconverted dimethyl ether and unconverted synthesis gas. The unconverted dimethyl ether and unconverted synthesis gas are withdrawn from condenser 24 through line 25 and are recycled to carbonylation and hydrogenolysis reactor 21.

The ethanol, methanol, methyl acetate, and ethyl acetate are withdrawn from condenser 24 through line 26 and passed to distillation column 27. Ethanol is recovered from distillation column 27 through line 29.

The methanol, methyl acetate, and ethyl acetate are withdrawn from distillation column 27 through line 28 and passed to distillation column 30. In distillation column 30, methanol is separated from the methyl acetate and ethyl acetate, and is withdrawn from distillation column 30 through line 31. If desired, the methanol can be recycled to dimethyl ether reactor 12.

The methyl acetate and ethyl acetate are withdrawn from distillation column 30 through line 32, and are recycled to the carbonylation and hydrogenolysis reactor 21.

The disclosures of all patents and publications (including published patent applications) are incorporated herein by reference to the same extent as if each patent and publication were incorporated individually by reference.

It is to be understood, however, that the scope of the present invention is not to be limited to the specific embodiments described above. The invention may be practiced other than as described particularly and still be within the scope of the accompanying claims.

What is claimed is:

1. A process for producing ethanol from synthesis gas, comprising:
   (a) reacting synthesis gas, said synthesis gas containing hydrogen and carbon monoxide, under conditions to provide a first reaction product including at least one ether, methanol, water, unreacted hydrogen, and unreacted carbon monoxide;
   (b) condensing said first reaction product to produce a first condensate stream comprising water and methanol and a second stream comprising said at least one ether, said unreacted hydrogen, said unreacted carbon monoxide, and water;
   (c) contacting said first condensate stream of step (b) with a desiccant, thereby removing water from said first condensate stream, thereby providing a stream comprising methanol;
   (d) contacting said second stream of step (b) with a desiccant, thereby removing water from said second stream of step (b), thereby providing a stream comprising said at least one ether, said unreacted hydrogen, and said unreacted carbon monoxide;
   (e) passing said stream comprising said at least one ether, said unreacted hydrogen, and said unreacted carbon monoxide of step (d) to a carbonylation/hydrogenolysis reactor, wherein said carbonylation/hydrogenolysis reactor contains a plurality of fixed catalyst beds, which contain said carbonylation catalyst and said hydrogenolysis catalyst, whereby said at least one ether, said unreacted hydrogen, and said unreacted carbon monoxide are reacted in the presence of a carbonylation catalyst selected from the group consisting of H-mordenite and Group VII metals, and a hydrogenolysis catalyst selected from the group consisting of copper chromite, copper oxide, and zinc oxide to provide a first ethanol product stream containing ethanol, methanol, methyl acetate, ethyl acetate, unconverted at least one ether, and unconverted synthesis gas;
   (f) condensing said first ethanol product stream to provide an ethanol condensate stream comprising ethanol, methanol, methyl acetate, and ethyl acetate, and an unconverted material stream comprising unconverted at least one ether and unconverted synthesis gas;
   (g) recycling said unconverted material stream of step (f) to step (e);
   (h) distilling said ethanol condensate stream to provide a second ethanol product stream comprising ethanol and a first distillate stream comprising methanol, methyl acetate, and ethyl acetate;
   (i) distilling said first distillate stream to produce a methanol stream comprising methanol and a second distillate stream comprising methyl acetate and ethyl acetate; and
   (j) recycling second distillate stream of step (i) to step (e).

2. The process of claim 1, and further comprising:
   recycling said stream comprising methanol of step (c) to step (a).

3. The process of claim 1, and further comprising:
   recycling said methanol stream of step (i) to step (a).

4. The process of claim 1 wherein said hydrogen and said carbon monoxide of said synthesis gas of step (a) are reacted at a pressure of from about 250 psi to about 2,000 psi.

5. The process of claim 4 wherein said hydrogen and said carbon monoxide of said synthesis gas of step (a) are reacted at a pressure of from about 300 psi to about 900 psi.

6. The process of claim 1 wherein said hydrogen and said carbon monoxide of said synthesis gas of step (a) are reacted at a temperature of from about 100° C. to about 400° C.

7. The process of claim 6 wherein said hydrogen and said carbon monoxide of said synthesis gas of step (a) are reacted at a temperature of from about 150° C. to about 350° C.

8. The process of claim 1 wherein said hydrogen and said carbon monoxide are reacted in step (a) at a molar ratio of hydrogen to carbon monoxide of from about 0.6 to about 3.0.

9. The process of claim 1 wherein said at least one ether is dimethyl ether.

10. The process of claim 1 wherein step (a) comprises:
(i) reacting said hydrogen with said carbon monoxide of said synthesis gas to produce methanol; and
(ii) converting said methanol to said at least one ether, thereby providing said first reaction product including said at least one ether, said unreacted hydrogen, said unreacted carbon monoxide, unreacted methanol, and water.

11. The process of claim 10 wherein step (a) is conducted in the presence of a catalyst.

12. The process of claim 11 wherein said catalyst is selected from the group consisting of copper chromite, copper oxide, zinc oxide, and mixtures thereof.

13. The process of claim 12 wherein said catalyst is supported on a support selected from the group consisting of alumina and zeolites.

14. The process of claim 12 wherein said catalyst further includes a transition metal.

15. The process of claim 1 wherein step (e) comprises:
(i) reacting said at least one ether with carbon monoxide to produce at least one acetate comprising methyl acetate and ethyl acetate; and
(ii) subjecting said at least one acetate to hydrogenolysis to produce ethanol and methanol.

16. The process of claim 9 wherein, in step (e), said carbon monoxide and said dimethyl ether are fed to said carbonylation/hydrogenolysis reactor at a molar ratio of carbon monoxide to dimethyl ether of from about 1:1 to about 20:1.

17. The process of claim 16 wherein, in step (e), said carbon monoxide and said dimethyl ether are fed to said carbonylation/hydrogenolysis reactor at a molar ratio of carbon monoxide to dimethyl ether of from about 5:1 to about 10:1.

18. The process of claim 9 wherein, in step (e), said hydrogen and said dimethyl ether are fed to said carbonylation/hydrogenoysis reactor at a molar ratio of hydrogen to dimethyl ether of from about 1:1 to about 20:1.

19. The process of claim 18 wherein, in step (e), said hydrogen and said dimethyl ether are fed to said carbonylation/hydrogenolysis reactor at a molar ratio of hydrogen to dimethyl ether of from about 5:1 to about 10:1.

20. The process of claim 1 wherein, in step (e), carbon monoxide is fed to said carbonylation/hydrogenolysis reactor at a gas hourly space velocity of from about 250 l/hr. to about 20,000 l/hr. per liter of catalyst.

21. The process of claim 20 wherein, in step (e), said carbon monoxide is fed to said carbonylation/hydrogenolysis reactor at a gas hourly space velocity of from about 2,000 l/hr. to about 8,000 l/hr. per liter of catalyst.

22. The process of claim 1, wherein, in step (e), said hydrogen and said carbon monoxide are fed to said carbonylation/hydrogenolysis reactor at a molar ratio of hydrogen to carbon monoxide of from about 0.6 to about 3.0.

* * * * *